United States Patent
Lynch et al.

(10) Patent No.: US 11,779,415 B2
(45) Date of Patent: Oct. 10, 2023

(54) SYSTEM AND METHOD FOR RAPID HALT AND RECOVERY OF MOTION DEVIATIONS IN REPOSITIONABLE ARMS

(71) Applicant: INTUITIVE SURGICAL OPERATIONS, INC., Sunnyvale, CA (US)

(72) Inventors: Goran A. Lynch, Oakland, CA (US); Paul G. Griffiths, Santa Clara, CA (US); Michael Turner, Sunnyvale, CA (US)

(73) Assignee: INTUITIVE SURGICAL OPERATIONS, INC., Sunnyvale, CA (US)

( * ) Notice: Subject to any disclaimer, the term of this patent is extended or adjusted under 35 U.S.C. 154(b) by 0 days.

(21) Appl. No.: 17/569,405

(22) Filed: Jan. 5, 2022

(65) Prior Publication Data

US 2022/0125532 A1  Apr. 28, 2022

Related U.S. Application Data (63) Continuation of application No. 16/069,875, filed as application No. PCT/US2016/067755 on Dec. 20, 2016, now Pat. No. 11,246,669.
(Continued)

(51) Int. Cl.
*A61B 34/32* (2016.01)
*A61B 34/30* (2016.01)
(Continued)

(52) U.S. Cl.
CPC ........ *A61B 34/32* (2016.02); *A61B 17/00234* (2013.01); *A61B 34/30* (2016.02);
(Continued)

(58) Field of Classification Search
CPC .......... A61B 34/32; A61B 34/30; A61B 17/30; A61B 2034/2059; A61B 2090/508;
(Continued)

(56) References Cited

U.S. PATENT DOCUMENTS

| 5,427,097 A | 6/1995 | Depp |
| 7,720,322 B2 | 5/2010 | Prisco et al. |

(Continued)

FOREIGN PATENT DOCUMENTS

| CN | 103957814 A | 7/2014 |
| JP | S6224305 A | 2/1987 |

(Continued)

OTHER PUBLICATIONS

Extended European Search Report for Application No. 16886793.5 dated Aug. 21, 2019, 11 pages.
(Continued)

*Primary Examiner* — Carl H Layno
*Assistant Examiner* — Michael J Lau
(74) *Attorney, Agent, or Firm* — Artegis Law Group, LLP (57) ABSTRACT

A computer-assisted device includes a first repositionable arm configured to support a first end effector, a second repositionable arm configured to support a second end effector, and a control unit. The control unit configured to monitor an actual motion of at least one structure selected from the group consisting of the first repositionable arm and the first end effector, determine a deviation threshold based on at least one parameter selected from the group consisting of a mode of operation of the first end effector and a mode of operation of the computer-assisted device, and in response to determining that the actual motion of the at least one structure deviates from a desired motion of the at least one structure by more than the deviation threshold, halt motion of the first repositionable arm and the first end
(Continued)

effector or halt motion of the second repositionable arm and the second end effector.

20 Claims, 5 Drawing Sheets

Related U.S. Application Data (60) Provisional application No. 62/281,142, filed on Jan. 20, 2016.

(51) Int. Cl.
| | |
|---|---|
| *A61B 17/00* | (2006.01) |
| *B25J 9/16* | (2006.01) |
| *A61B 90/50* | (2016.01) |
| *A61B 34/20* | (2016.01) |

(52) U.S. Cl.
CPC ... *B25J 9/1664* (2013.01); *A61B 2017/00123* (2013.01); *A61B 2017/00991* (2013.01); *A61B 2034/2059* (2016.02); *A61B 2090/508* (2016.02)

(58) Field of Classification Search
CPC . A61B 2017/00123; A61B 2017/00991; B25J 9/1664
USPC .............................................................. 606/1
See application file for complete search history.

(56) References Cited

U.S. PATENT DOCUMENTS

| | | | |
|---|---|---|---|
| 8,004,229 B2 | 8/2011 | Nowlin et al. | |
| 9,198,730 B2 | 12/2015 | Prisco et al. | |
| 9,295,524 B2 | 3/2016 | Schena et al. | |
| 11,246,669 B2* | 2/2022 | Lynch | A61B 17/00234 |
| 2005/0226377 A1 | 10/2005 | Wong et al. | |
| 2006/0058919 A1* | 3/2006 | Sommer | A61B 34/30 |
| | | | 700/245 |
| 2006/0108960 A1 | 5/2006 | Tanaka et al. | |
| 2006/0167440 A1 | 7/2006 | Cooper et al. | |
| 2007/0142825 A1* | 6/2007 | Prisco | A61B 34/70 |
| | | | 606/1 |
| 2007/0156122 A1 | 7/2007 | Cooper | |
| 2007/0282311 A1 | 12/2007 | Scott et al. | |
| 2008/0051631 A1 | 2/2008 | Dejima et al. | |
| 2008/0188890 A1 | 8/2008 | Weitzner et al. | |
| 2008/0212840 A1 | 9/2008 | Shalom et al. | |
| 2009/0024142 A1 | 1/2009 | Ruiz Morales | |
| 2009/0088775 A1* | 4/2009 | Swarup | A61B 34/71 |
| | | | 700/264 |
| 2010/0069833 A1* | 3/2010 | Wenderow | A61M 25/0147 |
| | | | 604/95.01 |
| 2010/0069920 A1 | 3/2010 | Naylor et al. | |
| 2010/0331859 A1 | 12/2010 | Omori | |
| 2011/0082587 A1 | 4/2011 | Ziaei et al. | |
| 2012/0101508 A1* | 4/2012 | Wook Choi | B25J 9/1697 |
| | | | 700/259 |
| 2012/0165829 A1 | 6/2012 | Chen et al. | |
| 2013/0024024 A1 | 1/2013 | Namiki | |
| 2013/0225963 A1 | 8/2013 | Kodandaramaiah et al. | |
| 2013/0331826 A1 | 12/2013 | Steege | |
| 2014/0005684 A1* | 1/2014 | Kim | G16H 20/40 |
| | | | 606/130 |
| 2014/0039517 A1 | 2/2014 | Bowling et al. | |
| 2014/0163736 A1* | 6/2014 | Azizian | B25J 9/1676 |
| | | | 700/259 |
| 2014/0222207 A1 | 8/2014 | Bowling et al. | |
| 2014/0228857 A1 | 8/2014 | Kodandaramaiah et al. | |
| 2014/0228862 A1 | 8/2014 | Inoue et al. | |
| 2014/0276948 A1* | 9/2014 | Zirps | A61B 34/35 |
| | | | 606/130 |
| 2014/0297130 A1 | 10/2014 | Griffiths et al. | |
| 2014/0316433 A1 | 10/2014 | Navve et al. | |
| 2015/0100066 A1* | 4/2015 | Kostrzewski | A61B 34/30 |
| | | | 606/130 |
| 2015/0257840 A1 | 9/2015 | Mohr et al. | |
| 2015/0359597 A1 | 12/2015 | Gombert et al. | |
| 2015/0374446 A1 | 12/2015 | Malackowski et al. | |
| 2016/0345929 A1 | 12/2016 | Azizian et al. | |
| 2018/0049792 A1 | 2/2018 | Eckert et al. | |
| 2019/0008599 A1 | 1/2019 | Lynch et al. | |
| 2020/0163539 A1 | 5/2020 | Diolaiti | |

FOREIGN PATENT DOCUMENTS

| | | |
|---|---|---|
| JP | S63207578 A | 8/1988 |
| JP | H08504347 A | 5/1996 |
| JP | H08141978 A | 8/1996 |
| JP | H08280695 A | 10/1996 |
| JP | H0966056 A | 3/1997 |
| JP | 2000300579 A | 10/2000 |
| JP | 2009525098 A | 7/2009 |
| JP | 2015003357 A | 1/2015 |
| WO | WO-2011118074 A1 | 9/2011 |
| WO | WO-2012166815 A1 | 12/2012 |
| WO | WO-2013063523 A1 | 5/2013 |
| WO | WO-2015120008 A1 | 8/2015 |
| WO | WO-2015142512 A1 | 9/2015 |
| WO | WO-2015142943 A1 | 9/2015 |

OTHER PUBLICATIONS

International Search Report and Written Opinion for Application No. PCT/US2016/067755, dated Apr. 10, 2017, 26 pages.

Vertut, J, and Coiffet P., "Robot Technology: Teleoperation and Robotics Evolution and Development," English translation, Prentice-Hall, Inc. Inglewood Cliffs, NJ, USA 1986, vol. 3A, 332 pages.

\* cited by examiner

SYSTEM AND METHOD FOR RAPID HALT AND RECOVERY OF MOTION DEVIATIONS IN REPOSITIONABLE ARMS

RELATED APPLICATIONS

This patent application is a continuation of U.S. patent application Ser. No. 16/069,875 (filed on Jul. 12, 2018), now U.S. Pat. No. 11,246,669, which is a U.S. National Stage patent application of International Patent Application No. PCT/US2016/067755 (filed on Dec. 20, 2016), the benefit of which is claimed, and claims priority to and the benefit of the filing date of U.S. Provisional Patent Application 62/281,142, entitled "SYSTEM AND METHOD FOR RAPID HALT AND RECOVERY OF MOTION DEVIATIONS IN MEDICAL DEVICE REPOSITIONABLE ARMS" filed Jan. 20, 2016, each of which is incorporated by reference herein in its entirety.

TECHNICAL FIELD

The present disclosure relates generally to operation of medical devices with repositionable arms and more particularly to rapid halt and recovery of the repositionable arms when motion deviations above a threshold are detected.

BACKGROUND

More and more devices are being replaced with autonomous and semiautonomous devices. This is especially true in the hospitals of today with large arrays of autonomous and semiautonomous medical devices being found in operating rooms, interventional suites, intensive care wards, emergency rooms, and/or the like. For example, glass and mercury thermometers are being replaced with electronic thermometers, intravenous drip lines now include electronic monitors and flow regulators, and traditional hand-held surgical instruments are being replaced by computer-assisted medical devices.

These computer-assisted medical devices provide both advantages and challenges to the personnel operating them. One of the many advantages of these computer-assisted medical devices is the flexibility in operating modes used to support different operations and procedures. For example, computer-assisted medical devices with one or more repositionable arms and/or end effectors often support several modes for controlling the position and/or orientation (i.e., the pose) of the repositionable arms and/or end effectors. In one possible mode, one or more of the repositionable arms and/or end effectors are operated via teleoperation using one or more input controls at an operator workstation and/or on the repositionable arms to control the motion and/or operation of the repositionable arms and/or the end effectors. In another possible mode, one or more of the repositionable arms and/or end effectors are operated autonomously or semi-autonomously by the computer-assisted medical device in order to execute a motion plan. In some examples, the motion plan may optionally include holding a pose of a repositionable arm and/or end effector so that no motion takes place. Examples of such computer-assisted medical devices that support these modes of operation include the da Vinci® Surgical System commercialized by Intuitive Surgical, Inc. of Sunnyvale, Calif.

During operation of the computer-assisted medical device, it is important for the computer-assisted medical device to monitor the actual motion being performed by the repositionable arms and/or end effectors to determine whether any of the repositionable arms and/or end effectors deviates beyond a reasonable threshold from an expected motion of the repositionable arm and/or end effector. This monitoring is often especially important for any portion of an end effector that is inserted into the interior anatomy of patient, as even small deviations in the motion of the end effector could damage tissue, such as an internal organ.

In some embodiments, the amount of monitoring and/or the sensitivity in the monitoring of the motion may optionally vary between the different control modes of the respective repositionable arm and/or end effector. For example, repositionable arms and/or end effectors that are being teleoperated by medical personnel using the input controls at the operator workstation and/or by medical personnel using the input controls on the repositionable arm can sometimes be monitored by the medical personnel, who are able to observe motion deviations and correct for them using the input controls. However, sometimes parts or all of the repositionable arms and/or end effectors being teleoperated by medical personnel cannot be adequately monitored by the medical personnel. The medical personnel may not be observing parts of the repositionable arms and/or end effectors during operation, lack sufficient knowledge or experience to anticipate the movements of the repositionable arms and/or end effectors, and the like. Further, repositionable arms and/or end effectors that are being autonomously and/or semi-autonomously controlled, including those repositionable arms and/or end effectors that are being held in place, are often not being observed or not being observed as closely by medical personnel so that motion deviations are less likely to be detected and/or compensated for by the medical personnel. Consequently, it is important for the computer-assisted medical device to actively monitor for motion deviations in the autonomously and/or semi-autonomously controlled repositionable arms and/or end effectors.

Motion deviations in the repositionable arms and/or end effectors can occur from many possible sources. In some examples, a motion deviation can occur due to a collision between two or more repositionable arms and/or end effectors. In some examples, a motion deviation can occur due to a collision between a repositionable arm and/or an end effector and other objects or structures external to the computer-assisted medical device. These other objects or structures may include other medical devices, a surgical table, medical personnel, anatomy of the patient, and/or the like. In some examples, the motion deviation can occur due to range of motion limits in the repositionable arm and/or end effector.

A common strategy for dealing with motion deviations is to place the computer-assisted medical device in a full emergency stop mode, such as by triggering a system-wide error condition. In the full emergency stop mode, motion of all of the repositionable arms and/or end effectors is stopped and further motion is not allowed again until medical personnel execute an often lengthy recovery procedure. And while this approach tends to maximize safety, it is often more disruptive than is often desirable because, for example, medical personnel are often capable of compensating for motion deviations in the teleoperated repositionable arms and/or end effectors and/or determining when the full-stop mode should be initiated.

Accordingly, it would be advantageous to have systems and methods that provide for a more measured response to motion deviations in autonomously and/or semi-autonomously controlled repositionable arms and/or end effectors.

SUMMARY

Advantageously, systems and methods in accordance with embodiments of the present invention allow for a rapid and/or measured response when a motion deviation above a desired threshold in a repositionable arm and/or end effector is detected. In one aspect, when a motion deviation above the desired threshold is detected, movement of each of the teleoperated, autonomously controlled, or semi-autonomously controlled repositionable arms and/or end effectors, including each repositionable arm and/or end effector that is being held in position, is halted and one or more medical personnel are notified of the halt. Once the condition causing the halt is cleared by the one or more medical personnel, teleoperated, autonomous, and/or semi-autonomous control of each of the repositionable arms and/or end effectors is allowed to resume. In some aspects, the methods used to halt the repositionable arms and/or end effectors vary based on types of the respective actuators used to permit the repositioning of the repositionable arms and/or end effectors. For example, brakes are applied to non-actuated repositionable elements, actuated repositionable elements with brakes have the brakes applied, and set points and/or feedback gains for the control algorithms for the actuated repositionable elements are changed. In some examples, the set points and/or feedback gains for position, velocity, torque, and/or the like may optionally be changed depending upon the desired halt behavior. In some examples, feed-forward torque may optionally be applied to maintain active gravity and/or inertial compensation in the repositionable arms and/or end effectors. In some aspects, the computer-assisted medical device may optionally provide instructions to the one or more medical personnel on how to clear the condition causing the halt.

In some aspects, use of the halt and recovery processes may optionally be limited to certain operating modes of the computer-assisted medical device, the repositionable arms, and/or the end effectors. In some examples, the halt and recovery processes are optionally used when a repositionable arm and/or an end effector is being operated in a null space mode where a pose of the end effector is not expected to change even though redundant degrees of freedom in the repositionable arm proximal to the end effector are being manipulated to reposition a portion of the repositionable arm. In some examples, the halt and recovery processes are optionally used when a repositionable arm and/or end effector are being operated in an instrument removal mode where the end effector is being removed from a patient and/or is disconnected from a cannula where the end effector is inserted into the patient.

Consistent with some embodiments, a computer-assisted medical device includes a first repositionable arm having one or more first repositionable elements for positioning the first repositionable arm (and a first end effector when the first end effector is mounted to the first repositionable arm), a second repositionable arm having one or more second repositionable elements for positioning the second repositionable arm (and a second end effector when the second end effector is mounted to the second repositionable arm), and a control unit communicably coupled to the first repositionable arm and the second repositionable arm. The control unit is configured to control motion of the first repositionable arm and the first end effector, monitor an actual motion of the first repositionable arm and the first end effector, determine whether the actual motion deviates from a desired motion of the first repositionable arm and the first end effector by more than a predetermined threshold, and halt motion of the first repositionable arm and the first end effector, or of the second repositionable arm and the second end effector, when the actual motion deviates from the desired motion by more than the predetermined threshold.

Consistent with some embodiments, a method of operating a computer-assisted medical device includes controlling, by a control unit of the computer-assisted medical device, motion of a first repositionable arm and a first end effector. The first repositionable arm includes one or more first repositionable elements for positioning the first repositionable arm and the first end effector is mounted to the first repositionable arm. The method further includes: monitoring, by the control unit, an actual motion of the first repositionable arm and the first end effector; determining, by the control unit, whether the actual motion deviates from a desired motion of the first repositionable arm and the first end effector by more than a predetermined threshold; and halting, by the control unit, motion of a second repositionable arm and a second end effector when the actual motion deviates from the desired motion by more than the predetermined threshold. The second repositionable arm includes one or more second repositionable elements for positioning the second repositionable arm, and the second end effector is mounted to the second repositionable arm.

Consistent with some embodiments, a non-transitory machine-readable medium including a plurality of machine-readable instructions which when executed by one or more processors associated with a computer-assisted medical device are adapted to cause the one or more processors to perform a method. The method includes controlling motion of a first repositionable arm and a first end effector. The first repositionable arm includes one or more first repositionable elements for positioning the first repositionable arm and the first end effector is mounted to the first repositionable arm. The method further includes monitoring an actual motion of the first repositionable arm and the first end effector, determining whether the actual motion deviates from the desired motion by more than a predetermined threshold and, halting motion of a second repositionable arm and a second end effector when the actual motion deviates from the desired motion by more than the predetermined threshold. The second repositionable arm includes one or more second repositionable elements for positioning the second repositionable arm and the second end effector is mounted to the second repositionable arm.

Consistent with some embodiments, a computer-assisted medical device includes a repositionable arm, an input device, and a control unit. The repositionable arm has one or more repositionable elements for positioning the repositionable arm and an end effector. The control unit is coupled to the repositionable arm and the input device, and is configured to receive a command from the input device, wherein the command indicates a desired motion of the repositionable arm and the end effector. The control unit is further configured to: monitor an actual motion of the repositionable arm and the end effector, determine whether the actual motion deviates from a desired motion of the repositionable arm and the end effector by more than a predetermined threshold, and halt motion of the repositionable arm and the end effector in response to the actual motion deviating from the desired motion by more than the predetermined threshold.

BRIEF DESCRIPTION OF THE DRAWINGS

In the figures, elements having the same designations have the same or similar functions.

DETAILED DESCRIPTION

In the following description, specific details are set forth describing some embodiments consistent with the present disclosure. It will be apparent to one skilled in the art, however, that some embodiments may be practiced without some or all of these specific details. The specific embodiments disclosed herein are meant to be illustrative but not limiting. One skilled in the art may realize other elements that, although not specifically described here, are within the scope and the spirit of this disclosure. In addition, to avoid unnecessary repetition, one or more features shown and described in association with one embodiment may be incorporated into other embodiments unless specifically described otherwise or if the one or more features would make an embodiment non-functional. The term "including" means including but not limited to, and each of the one or more individual items included should be considered optional unless otherwise stated. Similarly, the term "may" indicates that an item is optional.

Figure 1:
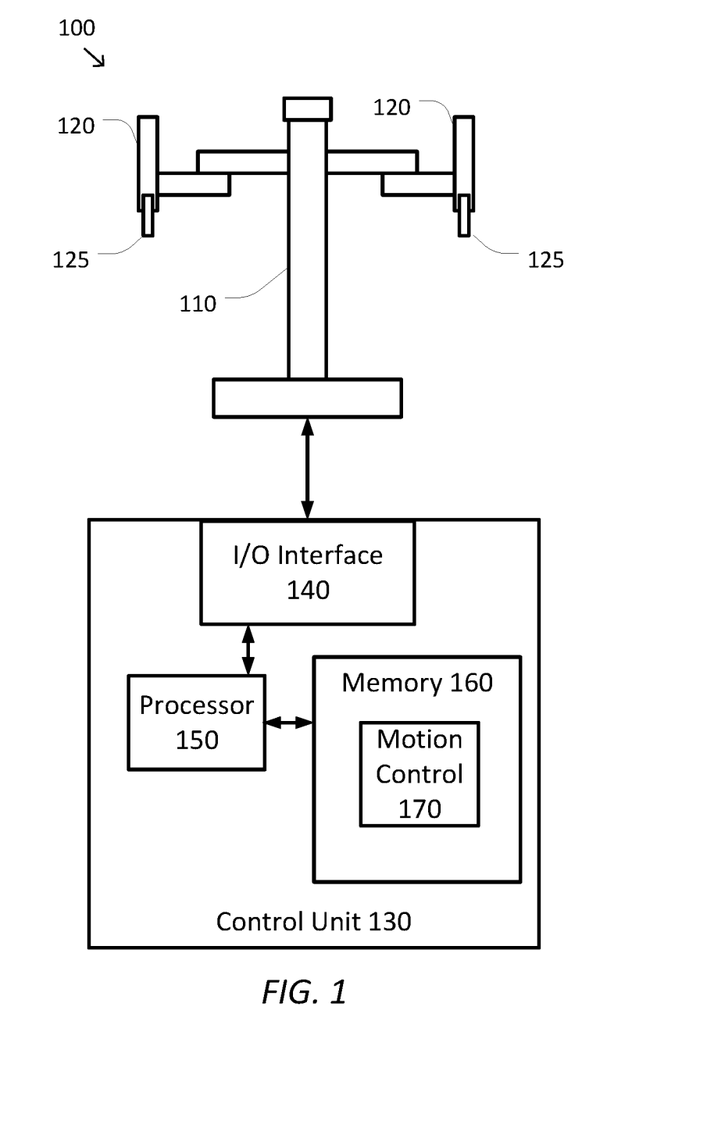
FIG. 1 is a simplified diagram of a computer-assisted system according to some embodiments.

FIG. 1 is a simplified diagram of a computer-assisted system 100 according to some embodiments. As shown in FIG. 1, computer-assisted system 100 includes a computer-assisted device 110 (also "patient side support system 110") with one or more repositionable arms 120. In some examples, each of the one or more repositionable arms 120 may optionally include one or more links and one or more joints with the one or more joints allowing articulation of the one or more links. In some examples, each of the one or more repositionable arms 120 may optionally include one or more flexible members, such as a steerable tube. Each of the one or more repositionable arms 120 supports one or more end effectors 125 that may optionally be mounted to a distal end of a respective one of the repositionable arms 120. In some examples, device 110 may be consistent with a computer-assisted medical device, such as a teleoperated surgical device. The one or more end effectors 125 include surgical instruments, imaging devices, and/or the like. In some examples, the surgical instruments include clamps, grippers, retractors, cautery tools, suction tools, suturing devices, and/or the like. In some examples, the imaging devices include stereoscopic and monoscopic imaging devices, imaging devices in the visible and infrared ranges, steerable endoscopic imaging devices, and/or the like. In some examples, each of the repositionable arms 120 and/or end effectors 125 may optionally be configured with a remote center of motion that maintains a stationary position in space even though links and/or joints of a corresponding repositionable arm 120 and/or end effector 125 proximal to the remote center of motion change a position or an orientation of the end effector 125 relative to the remote center of motion. In some examples, the remote center of motion may optionally correspond to a point where the corresponding repositionable arm 120 and/or end effector 125 is inserted through a body wall of a patient.

Computer-assisted device 110 is coupled to a control unit 130 via an input/output (I/O) interface 140. I/O interface 140 may optionally include one or more cables, connectors, ports, and/or buses, and it may optionally further include one or more networks with one or more network switching and/or routing devices. In some examples, I/O interface 140 may optionally include wireless interfaces. Control unit 130 includes a processor 150 coupled to memory 160 and to I/O interface 140. Operation of control unit 130 is controlled by processor 150. And although control unit 130 is shown with only one processor 150, it is understood that processor 150 is representative of one or more central processing units, multi-core processors, microprocessors, microcontrollers, digital signal processors, field programmable gate arrays (FPGAs), application specific integrated circuits (ASICs), and/or the like in control unit 130. Control unit 130 may optionally be implemented as a stand-alone subsystem and/or board added to a computing device or as a virtual machine. In some embodiments, control unit may optionally be included as part of an operator workstation (not shown) and/or operated separately from, but in coordination with the operator workstation. In some embodiments, computer-assisted device 110 and control unit 130 may optionally correspond to portions of a da Vinci® Surgical System commercialized by Intuitive Surgical, Inc. of Sunnyvale, Calif.

Memory 160 is used to store software executed by control unit 130 and/or one or more data structures used during operation of control unit 130. Memory 160 includes one or more types of machine readable media. Some common forms of machine readable media may include floppy disk, flexible disk, hard disk, magnetic tape, any other magnetic medium, CD-ROM, any other optical medium, punch cards, paper tape, any other physical medium with patterns of holes, RAM, PROM, EPROM, FLASH-EPROM, any other memory chip or cartridge, and/or any other medium from which a processor or computer is adapted to read.

As shown, memory 160 includes a motion control application 170 that supports autonomous, semiautonomous, and/or teleoperated control of computer-assisted device 110. Motion control application 170 includes one or more control modules for actuating the repositionable arms 120 and/or end effectors 125 so as to drive the repositionable arms 120 and/or end effectors 125 to desired poses based on the autonomous, semiautonomous, and/or teleoperated motion control strategy currently in use for the respective repositionable arm 120 and/or end effector 125. Motion control application 170 may optionally include one or more application programming interfaces (APIs) for receiving position, motion, and/or other sensor information from computer-assisted device 110 through I/O interface 140, exchanging position, motion, and/or collision avoidance information with other control units regarding other devices, such as a surgical table and/or imaging device, and/or planning and/or assisting in the planning of motion for computer-assisted device 110, repositionable arms 120, and/or end effectors 125 of computer-assisted device 110. In some embodiments, one or more registration markers, fiducial markers, and/or the like mounted on repositionable arms 120 and/or end effectors 125 may alternatively be tracked using one or more tracking sensors, such as an imaging device, to supplement and/or replace the sensor inputs to determine the post of the repositionable arms 120 and/or end effectors 125. Optionally, other position and shape sensing components are additionally and/or alternatively used, such as optical fiber shape sensors using Fiber Bragg Grating technology, such as the optical fiber shape sensors disclosed in U.S. Pat. No. 7,720, 322 entitled "Fiber Optic Shape Sensor," which is hereby incorporated by reference in its entirety.

And although motion control application 170 is depicted as a software application, motion control application 170 may be implemented using hardware, software, and/or a combination of hardware and software.

In some embodiments, computer-assisted system 100 may be found in an operating room and/or an interventional suite. And although computer-assisted system 100 includes only one computer-assisted device 110 with two repositionable arms 120, one of ordinary skill would understand that computer-assisted system 100 may include any number of other devices. Examples of other devices include additional computer-assisted devices with repositionable arms and/or end effectors of similar and/or different design from computer-assisted device 110. In some examples, each of the computer-assisted devices with repositionable arms and/or end effectors may include fewer or more repositionable arms and/or end effectors.

Figure 2:
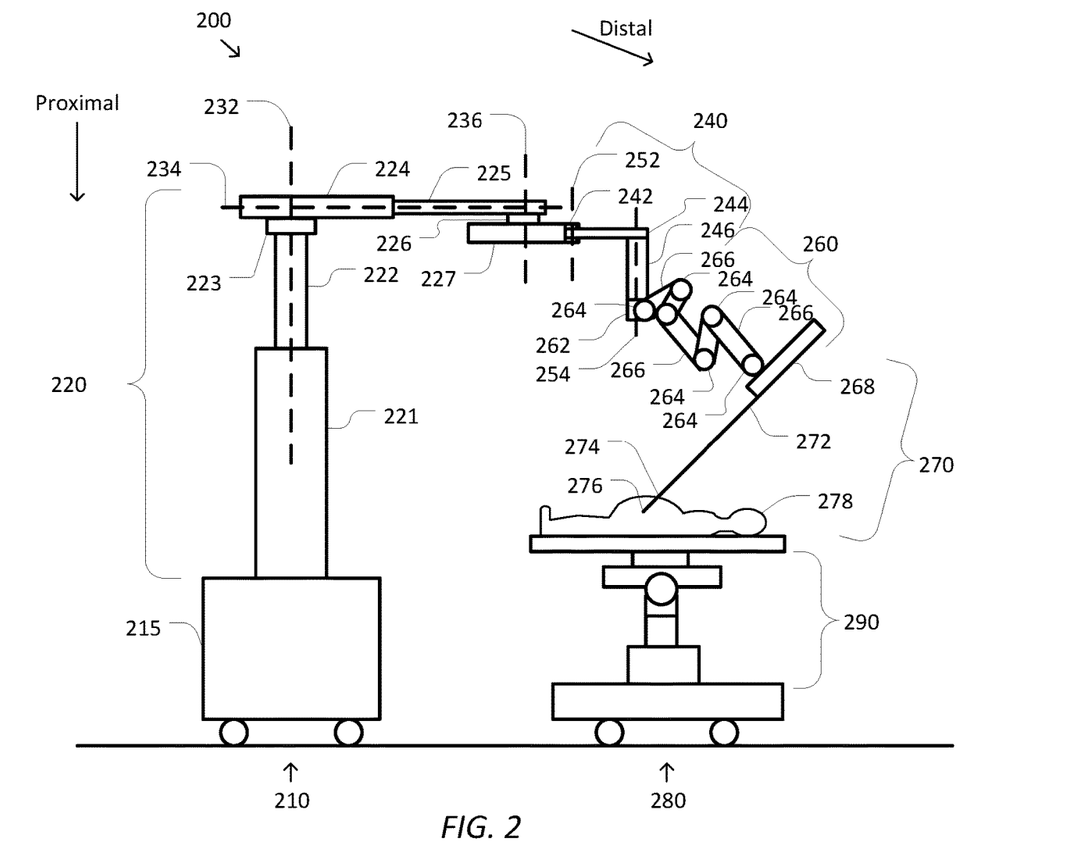
FIG. 2 is a simplified diagram showing a computer-assisted medical system according to some embodiments.

FIG. 2 is a simplified diagram showing a computer-assisted medical system 200 according to some embodiments. For example, the computer-assisted medical system 200 may be consistent with computer-assisted system 100. As shown in FIG. 2, the computer-assisted medical system 200 includes a computer-assisted medical device 210 with one or more repositionable arms. The computer-assisted medical system 200 is configured to work with a surgical table 280. Although not shown in FIG. 2, the computer-assisted medical device 210 and/or the surgical table 280 may be coupled together using one or more interfaces, such as I/O interface 140, and one or more control units, such as control unit 130, so that kinematic information about the computer-assisted medical device 210 is known to a motion control application, such as motion control application 170, being used to perform motion of the repositionable arms of the computer-assisted medical device 210. In some embodiments, the surgical table 280 is part of the computer-assisted medical system 200; in other embodiments, the surgical table 280 is not part of the computer-assisted medical system 200.

The computer-assisted medical device 210 includes various links and joints. In the embodiments of FIG. 2, the computer-assisted medical device 210 is generally divided into three different sets of links and joints. Starting at the proximal end, a mobile or mobile cart 215 acts as a mechanical ground for computer-assisted device 210. Mobile cart 215 may optionally be repositioned and/or re-oriented about surgical table 280 to support different procedures to be performed by computer-assisted medical device 210. Coupled to mobile cart 215 is a set-up structure 220. Coupled to a distal end of the set-up structure is a series of links and set-up joints 240, forming a repositionable arm of the articulated variety. And coupled to a distal end of the set-up joints 240 is a multi-jointed manipulator 260. In some examples, the series of set-up joints 240 and manipulator 260 may correspond to one of the repositionable arms 120. And although the computer-assisted device is shown with only one series of set-up joints 240 and a corresponding manipulator 260, one of ordinary skill would understand that the computer-assisted medical device 210 may optionally include more than one series of set-up joints 240 and multiple corresponding manipulators 260 so that the computer-assisted medical device 210 is equipped with multiple repositionable arms.

As shown, the computer-assisted medical device 210 is mounted on the mobile cart 215. The mobile cart 215 enables the computer-assisted medical device 210 to be transported from location to location, such as between operating rooms or within an operating room to better position the computer-assisted device in proximity to the surgical table 180. The set-up structure 220 is mounted on the mobile cart 215. As shown in FIG. 2, the set-up structure 220 includes a two part column including column links 221 and 222. Coupled to the upper or distal end of the column link 222 is a shoulder joint 223. Coupled to the shoulder joint 223 is a two-part boom including boom links 224 and 225. At the distal end of the boom link 225 is a wrist joint 226, and coupled to the wrist joint 226 is an arm mounting platform 227.

The links and joints of the set-up structure 220 include various degrees of freedom for changing the position and orientation (i.e., the pose) of the arm mounting platform 227. For example, the two-part column is used to adjust a height of the arm mounting platform 227 by moving the shoulder joint 223 up and down along an axis 232. The arm mounting platform 227 is additionally rotated about the mobile cart 215, the two-part column, and the axis 232 using the shoulder joint 223. The horizontal position of the arm mounting platform 227 is adjusted along an axis 234 using the two-part boom. And the orientation of the arm mounting platform 227 may also be adjusted by rotation about an arm mounting platform orientation axis 236 using the wrist joint 226. Thus, subject to the motion limits of the links and joints in the set-up structure 220, the position of the arm mounting platform 227 may be adjusted vertically above the mobile cart 215 using the two-part column. The positions of the arm mounting platform 227 may optionally be adjusted radially and angularly about the mobile cart 215 using the two-part boom and the shoulder joint 223, respectively. And the angular orientation of the arm mounting platform 227 may optionally be changed using the wrist joint 226.

The arm mounting platform 227 is used as a mounting point for one or more repositionable arms. The ability to adjust the height, horizontal position, and orientation of the arm mounting platform 227 about the mobile cart 215 provides a flexible set-up structure for positioning and orienting the one or more repositionable arms about a work space located near the mobile cart 215 where an operation or procedure is to take place. For example, arm mounting platform 227 may be positioned above a patient so that the various repositionable arms and their corresponding manipulators and instruments have sufficient range of motion to perform a surgical procedure on the patient. FIG. 2 shows a single repositionable arm coupled to the arm mounting platform 227 using a first set-up joint 242. And although only one repositionable arm is shown, one of ordinary skill would understand that two, three, four, or even more repositionable arms may be coupled to the arm mounting platform 227 using additional first set-up joints.

The first set-up joint 242 forms the most proximal portion of the set-up joints 240 section of the repositionable arm. The set-up joints 240 may further include a series of joints and links. As shown in FIG. 2, the set-up joints 240 include at least links 244 and 246 coupled via one or more joints (not expressly shown). The joints and links of the set-up joints 240 include the ability to rotate the set-up joints 240 relative to the arm mounting platform 227 about an axis 252 using the first set-up joint 242, adjust a radial or horizontal distance between the first set-up joint 242 and the link 246, adjust a height of a manipulator mount 262 at the distal end of link 246 relative to the arm mounting platform 227 along an axis 254, and rotate the manipulator mount 262 about axis 254. In some examples, the set-up joints 240 may optionally further include additional joints, links, and axes permitting additional degrees of freedom for altering a pose of the manipulator mount 262 relative to the arm mounting platform 227.

The manipulator 260 is coupled to the distal end of the set-up joints 240 via the manipulator mount 262. The manipulator 260 includes additional joints 264 and links 266 with an instrument carriage 268 mounted at the distal end of the manipulator 260. An instrument 270 is mounted to the instrument carriage 268. Instrument 270 includes a shaft 272, which is aligned along an insertion axis. The shaft 272 is typically aligned so that it passes through a remote center of motion 274 associated with the manipulator 260. Location of the remote center of motion 274 is typically maintained in a fixed translational relationship relative to the manipulator mount 262 so that operation of the joints 264 in the manipulator 260 result in rotations of the shaft 272 about the remote center of motion 274. Depending upon the embodiment, the fixed translational relationship of the remote center of motion 274 relative to the manipulator mount 262 is maintained using physical constraints in the joints 264 and links 266 of the manipulator 260, using software constraints placed on the motions permitted for the joints 264, and/or a combination of both. Representative embodiments of computer-assisted surgical devices using remote centers of motion maintained using physical constraints in joints and links are described in U.S. patent application Ser. No. 13/906,888 entitled "Redundant Axis and Degree of Freedom for Hardware-Constrained Remote Center Robotic Manipulator," which was filed May 13, 2013, and representative embodiments of computer-assisted surgical devices using remote centers of motion maintained by software constraints are described in U.S. Pat. No. 8,004,229 entitled "Software Center and Highly Configurable Robotic Systems for Surgery and Other Uses," which was filed May 19, 2005, the specifications of which are hereby incorporated by reference in their entirety In some examples, the remote center of motion 274 may correspond to a location of a body opening, such as an incision site or body orifice, in a patient 278 where shaft 272 is inserted into the patient 278. Because the remote center of motion 274 corresponds to the body opening, as the instrument 270 is used, the remote center of motion 274 remains stationary relative to the patient 278 to limit stresses on the anatomy of the patient 278 at the remote center of motion 274. In some examples, the shaft 272 may be optionally passed through a cannula (not shown) located at the body opening. In some examples, instruments having a relatively larger shaft or guide tube outer diameter (e.g., 4-5 mm or more) may be passed through the body opening using a cannula and the cannula may optionally be omitted for instruments having a relatively smaller shaft or guide tube outer diameter (e.g., 2-3 mm or less).

At the distal end of the shaft 272 is an end effector 276. The degrees of freedom in the manipulator 260 due to the joints 264 and the links 266 may permit at least control of the roll, pitch, and yaw of the shaft 272 and/or the end effector 276 relative to the manipulator mount 262. In some examples, the degrees of freedom in the manipulator 260 may further include the ability to advance and/or withdraw the shaft 272 using the instrument carriage 268 so that the end effector 276 may be advanced and/or withdrawn along the insertion axis and relative to the remote center of motion 274. In some examples, the manipulator 260 may be consistent with manipulators for use with the da Vinci® Surgical System commercialized by Intuitive Surgical, Inc. of Sunnyvale, Calif. In some examples, the instrument 270 is a surgical instrument, an imaging device, and/or the like. In some examples, possible surgical instruments consistent with instrument 270 include clamps, grippers, retractors, cautery tools, suction tools, suturing devices, and/or the like. In some examples, possible imaging devices consistent with instrument 270 include stereoscopic and monoscopic imaging devices, imaging devices in the visible and infrared ranges, steerable endoscopic imaging devices, and/or the like. In some examples, the end effector 276 may include additional degrees of freedom, such as roll, pitch, yaw, grip, and/or the like that allow for additional localized manipulation of portions of the end effector 276 relative to the distal end of the shaft 272.

During a surgery or other medical procedure, the patient 278 is typically located on the surgical table 280. The surgical table 280 is typically located in proximity to mobile cart 215 so that the instrument 270 and/or end effector 276 may be manipulated by the computer-assisted medical device 210 while the shaft 272 of instrument 270 is inserted into the patient 278 at the body opening. The surgical table 280 may optionally include a repositionable structure 290 that includes one or more joints or links so that the relative location of the patient 278, relative to the mobile cart 215 is further controllable.

As discussed above and further emphasized here, FIG. 2 is merely an example which should not unduly limit the scope of the claims. One of ordinary skill in the art would recognize many variations, alternatives, and modifications. It should be understood that computer-assisted medical system 200 is shown for illustrational purposes only and that the various embodiments of this disclosure are equally applicable to computer-assisted systems of different designs and configurations. As one example, in some embodiments, computer-assisted medical device 210 may optionally be mechanically grounded in other ways than via mobile cart 215. In some examples, computer-assisted medical device 210 may optionally be mechanically grounded by mounting the computer-assisted medical device 210 to the surgical table 280, a wall of an operating room, a ceiling of the operating room, and/or any combination thereof. As another example, in some embodiments, computer-assisted medical device 210 has a different kinematic structure than shown in FIG. 2, comprising any appropriate number and types of joints, links, and other components, and having a different set of degrees of freedom. As yet a further example, in various embodiments, the computer-assisted medical device 210 comprises a single repositionable arm, multiple repositionable arms physically coupled to a single base, multiple repositionable arms grounded to different bases, etc.

Because end effector 276 and/or other portions of computer-assisted medical device 210 may be inserted into patient 278 and/or operated in proximity to patient 278, other medical devices such as surgical table 280, and/or medical personnel, it is important for the computer-assisted medical system 200 to monitor the current motion of computer-assisted medical device 210 and/or end effector 276 to determine whether any motion of the computer-assisted medical device 210 and/or end effector 276 deviates beyond a reasonable threshold from an expected motion. This monitoring is often especially important for any portion of end effector 276 that is inserted into patient 278, as even small deviations in the motion and thus the pose of end effector 276 could damage tissue, such as an internal organ, of patient 278. In some examples, detecting the deviation in motion includes monitoring kinematic and/or dynamic values associated with computer-assisted medical device 210 and/or end effector 276. In some examples, this may optionally include monitoring one or more of the actual position of the repositionable elements of computer-assisted medical device 210, rotations, and/or velocities of the actuators and/or repositionable elements of computer-assisted medical device 210, forces and/or torques applied by the actuators, and/or the like. In some examples, detecting the deviation may optionally include monitoring a motion plan for the computer-assisted medical device 210 to predictively determine whether an impending collision is likely.

In some embodiments, the amount of monitoring and/or the sensitivity in the monitoring of the various kinematic and/or dynamic values may optionally vary between the different control modes of the respective repositionable arms and/or end effectors of computer-assisted medical device 210. For example, repositionable arms and/or end effectors that are being teleoperated by medical personnel using input controls at an operator workstation and/or by medical personnel using input controls on a repositionable arm of computer-assisted device 210 are often being monitored by the medical personnel, who are able to observe motion deviations and correct for them using the input controls. In contrast, repositionable arms and/or end effectors that are being teleoperated, autonomously controlled, and/or semi-autonomously controlled, including those repositionable arms and/or end effectors that are being held in place with a stationary pose, are often not being observed or not being observed as closely by medical personnel so that motion deviations are less likely to be detected and/or compensated for by the medical personnel. Consequently, it is important for computer-assisted medical system 200 to actively monitor for motion deviations in the teleoperated, autonomously controlled, and/or semi-autonomously controlled repositionable arms and/or end effectors of computer-assisted medical device 210.

Motion deviations in the repositionable arms and/or end effectors can occur from many possible sources. In some examples, a motion deviation can occur due to a collision between two repositionable arms and/or end effectors of computer-assisted medical device 210. In some examples, a motion deviation can occur due to a collision between a repositionable arm and/or an end effector and other objects or structures located in proximity to computer-assisted medical device 210. These other objects or structures may include other medical devices, surgical table 280, medical personnel, anatomy of patient 278, and/or the like. In some examples, the motion deviation can occur due to range of motion limits in the computer-assisted medical device 210. In some examples, a deviation may optionally be predictively determined using a collision-avoidance approach that predicts a likelihood of an impending collision.

Once a motion deviation above a threshold is determined in a teleoperated, autonomously controlled, and/or semi-autonomously controlled repositionable arm and/or end effector 276, computer-assisted medical system 200 may be configured to place the computer-assisted medical device 210 in a mode that minimizes the possibility that the amount of motion deviation will increase. This helps prevent injury to patient 278, damage to computer-assisted medical device 210, damage to surgical table 280, damage to other medical devices, injury to medical personnel, and/or the like.

Figure 5:
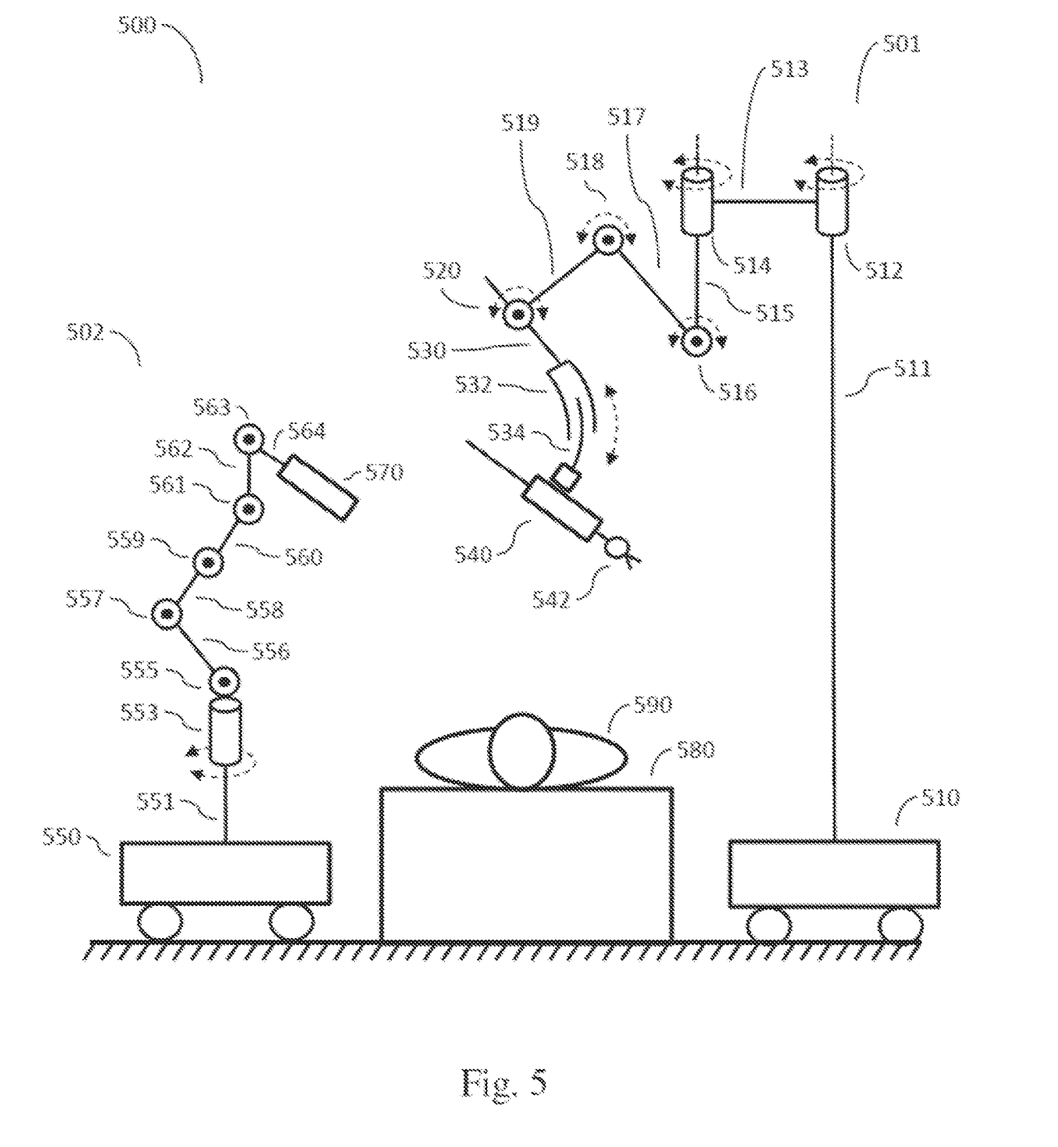
FIG. 5 is a simplified diagram showing a computer-assisted medical system according to some embodiments.

FIG. 5 is a simplified diagram showing a computer-assisted medical system 500 according to some embodiments. For example, the computer-assisted medical system 500 may be consistent with computer-assisted system 100. Thus, much of the previous discussion, including discussion associated with the computer-assisted medical systems 100, 200 are applicable to embodiments of the computer-assisted medical system 500.

As shown in FIG. 5, the computer-assisted medical system 500 includes a computer-assisted medical device comprising two repositionable arms 501, 502 mounted to two different bases 510, 550, respectively. The bases 510, 550 are moveable relative to each other and to a surgical table 280 designed to support a patient 590 during a medical procedure. The computer-assisted medical system is configured to work with the surgical table 280. The two repositionable arms 501, 502 may or may not be communicably coupled to the surgical table 580 in various embodiments.

Repositionable arm 501 is shown as a schematic, with a number of links and joints (six links 511, 513, 515, 517, 519, 530, five rotary joints 512, 514, 516, 518, 520, and no prismatic joints). A telescoping cannula mount system is located at the end of the repositionable arm 501. The telescoping cannula mount system comprises a cannula mount portion 534 that can be extended from or parked within a distal end portion 532 of the link 530. A cannula can be mounted to the cannula mount arm 1255, and a tool 540 can be extended through the cannula to perform operations. Examples of tools 540 include imaging devices such as endoscopes and tissue manipulation instruments such as graspers and staplers.

Repositionable arm 502 is also shown as a schematic, with a number of links and joints (six links 551, 556, 558, 560, 562, 564, six rotary joints 553, 555, 557, 559, 561, 563, and no prismatic joints). An imaging device 570 is shown mounted at the end of the link 564, and other embodiments may comprise a different tool, or the tool may be changed during operation.

Computer-assisted medical system 200 is shown for illustrational purposes only and is merely an example which should not unduly limit the scope of the claims. One of ordinary skill in the art would recognize many variations, alternatives, and modifications.

Figure 3:
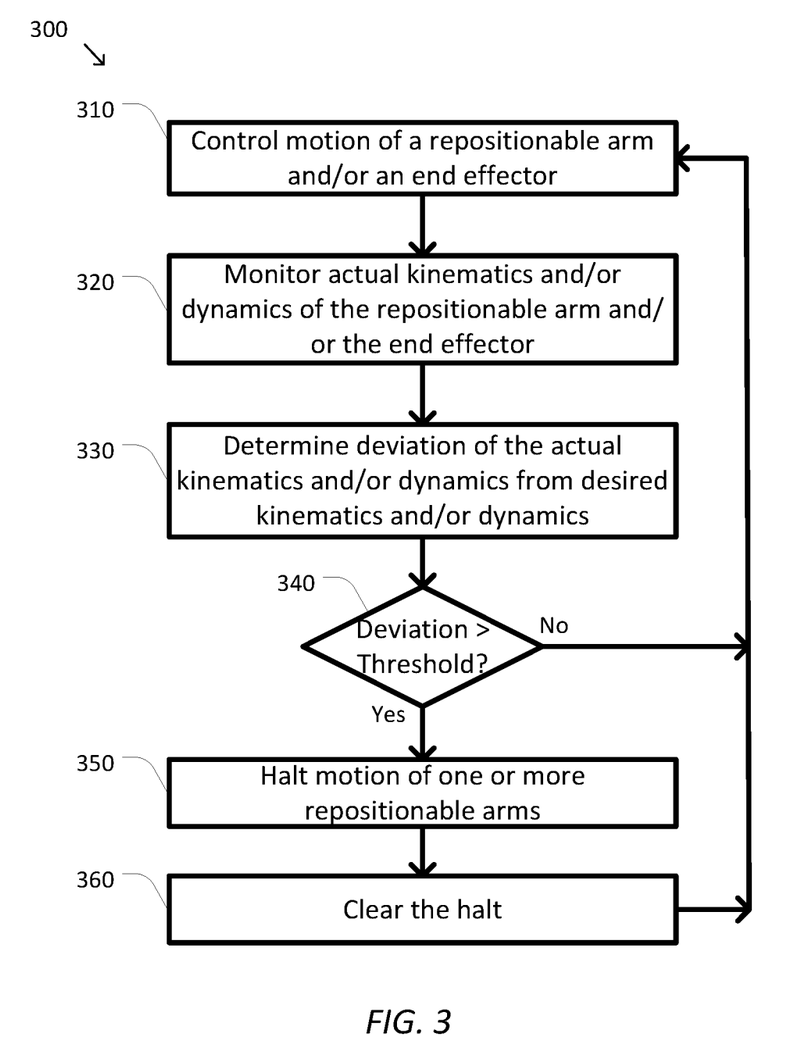
FIG. 3 is a simplified diagram of a method of rapid halting and recovery for a computer-assisted medical device according to some embodiments.

FIG. 3 is a simplified diagram of a method 300 of rapid halting and recovery for a computer-assisted medical device according to some embodiments. One or more of the processes 310-360 of method 300 may be implemented, at least in part, in the form of executable code stored on non-transient, tangible, machine readable media that when run by one or more processors (e.g., the processor 150 in control unit 130) may cause the one or more processors to perform one or more of the processes 310-360. In some embodiments, method 300 may optionally be used to monitor a computer-assisted medical device, such as computer-assisted medical device 210 to help ensure that undesirable deviations in motion of one or more of the repositionable arms and/or end effectors, such as end effector 276, are quickly and effectively detected and managed to reduce the likelihood of injury to a patient, injury to medical personnel, damage to the computer-assisted medical device, damage to other equipment, and/or the like. In some examples, use of method 300 may also optionally permit active continuation of teleoperation of one or more repositionable arms and/or end effectors of the computer-assisted medical device while appropriately halting one or more teleoperated, autonomously controlled, and/or semi-autonomously controlled repositionable arms and/or end effectors. In various embodiments, the computer-assisted medical device may change the mode of a repositionable arm and/or end effector to autonomous or semi-autonomous mode to halt its motion, or to resume its motion after halting its motion.

According to some embodiments, processes 310-340 are concurrently applied to each of the repositionable arms and/or end effectors of the computer-assisted medical device so that a deviation in the motion of any of the repositionable arms and/or end effectors that is above a threshold trigger the halting and recovery of processes 350 and 360. In some examples, application of processes 310-340 may optionally be limited to repositionable arms and/or end effectors operating in modes that are subject to the halting and recovery of processes 350 and 360. According to some embodiments, the order in which processes 310-360 are performed may optionally vary from the order implied by the diagram of FIG. 3. In some examples, processes 310-330 may optionally be performed concurrently. In some examples, process 350 and 360 may optionally be performed concurrently. In some examples, process 310-340 may optionally be performed continuously throughout method 300 so that repositionable arms and/or end effectors are continuously under control and monitoring by a computer-assisted medical system.

At a process 310, control of the motion of a repositionable arm and/or an end effector occurs. In general, each of the repositionable arms and/or end effectors of the computer-assisted medical device are being actively controlled at some level at all times. This includes even those repositionable arms and/or end effectors that are being held in place at a fixed pose (where the desired motion is no motion). This is because, holding a fixed pose may optionally include activating one or more brakes of the corresponding repositionable arm and/or end effector and/or applying inertia and/or gravity compensation that prevents changes in the pose of the corresponding repositionable arm and/or end effector due to forces applied to the corresponding arm and/or end effector due to gravity. Control of the motion of the repositionable arm and a corresponding end effector includes sending one or more signals, such as voltages, currents, pulse-width modulations, and/or the like to the one or more actuators used to control the one or more repositionable elements of the end effector and/or the repositionable arm and other structures used to manipulate the motion and thus the pose of the repositionable arm and/or the end effector. The one or more signals are then converted to forces and/or torques that effectuate the desired motion. In some examples, control of the repositionable arm and/or the end effector and the various actuators may optionally include control algorithms managing position, velocity, force, torque, and/or the like for the one or more repositionable elements of the end effector and/or the actuators. In some examples, one or more kinematic models for the repositionable arm, the end effector, and/or the computer-assisted medical device may optionally be used to covert desired motions into corresponding control signals for each of the actuators. For repositionable arms and/or end effectors under teleoperated control by medical personnel, the motion is optionally directed by the medical personnel using one or more input controls located at an operator console, on the computer-assisted medical device, and/or other suitable locations. For repositionable arms and/or end effectors under autonomous and/or semi-autonomous control, the motion is optionally directed by a motion plan for the repositionable arm and/or the end effector that optionally varies depending upon the desired autonomous or semi-autonomous motion. For repositionable arms and/or end effectors under teleoperation, the motion is optionally adjusted by the computer-assisted medical device depending upon the desired motion as indicated by a command into an input device used by a human operator.

At a process 320, actual kinematics and/or dynamics of the repositionable arm and/or the end effector are monitored. As the repositionable arm and/or the end effector is being controlled using process 310, the actual kinematics and/or dynamics of the repositionable arm and/or the end effector is monitored to help verify that the repositionable arm and/or the end effector are making the expected motion. In some examples, positional and/or rotational feedback sensors coupled to the actuators and/or one or more repositionable elements of the repositionable arm and/or the end effector are monitored. In some examples, this may optionally include monitoring one or more of the actual position of the repositionable elements, rotations, and/or velocities of the actuators and/or repositionable elements, forces and/or torques applied by the actuators, and/or the like. In some examples, the various repositionable element and/or actuator sensor readings may optionally be applied to the kinematic model of the repositionable arm and/or the end effector to determine the actual pose of the end effector. In some embodiments, one or more registration markers, fiducial markers, and/or the like mounted on the end effector and/or the repositionable arm may alternatively be tracked using one or more tracking sensors, such as an imaging device, to supplement and/or replace the sensors to determine the actual positions of the repositionable elements and/or the pose of the end effector. Optionally, other position and shape sensing components are additionally and/or alternatively used, such as optical fiber shape sensors using Fiber Bragg Grating technology, such as the optical fiber shape sensors disclosed in U.S. Pat. No. 7,720,322 entitled "Fiber Optic Shape Sensor," which is hereby incorporated by reference in its entirety.

In general, the actual pose of the end effector is determined based on the various degrees of freedom of motion available for the end effector. In some examples, the degrees of freedom may optionally include one or more of an x, y, and/or z spatial position of the end effector, a roll, pitch, and/or yaw orientation of the end effector, and/or one or more actuation degrees of freedom, such as opening angle of a jaw, position of a cutting blade, position of a staple actuating sled, and/or the like. In some examples, the pose may optionally include a composite of some or all of the degrees of freedom. For example, the monitoring of the actual pose may optionally be limited to the x, y, and z positional degrees of freedom and ignore the orientation and/or actuation degrees of freedom.

At a process 330, a deviation of the actual kinematics and/or dynamics of the repositionable arm and/or the end effector from desired kinematics and/or dynamics of the repositionable arm and/or the end effector is determined. Using the actual kinematics and/or dynamics of the repositionable arm and/or the end effector determined during process 320 and the desired kinematics and/or dynamics of the repositionable arm and/or the end effector that is being commanded to control the motion of the repositionable arm and/or the end effector by process 310, a deviation between the actual kinematics and/or dynamics and the desired kinematics and/or dynamics is determined. In some examples, the deviation is optionally determined separately for each of the kinematic and/or dynamic values (e.g., the positions, rotations, velocities, forces, torques, and/or poses) monitored during process 320 being monitored during process 320. In some examples, the deviation is optionally determined by measuring a composite deviation, such as a root-mean-square (RMS) error, between the actual kinematic and/or dynamic values and their corresponding desired values. In some examples, when the monitoring of process 320 is limited to the actual position of the end effector, the deviation corresponds to the physical distance between the actual position and the desired position of the end effector. In some examples, each of the values monitored during process 320 may optionally be weighted to place more or less emphasis on one or more of the values. In some examples, higher weight, and thus emphasis, may optionally be placed on the position of the end effector than on the orientation of the end effector. In some examples, higher weight may optionally be placed on position, rotation, velocity, force and/or torque values for repositionable elements located more proximally on the kinematic chain for the repositionable arm as they may be more likely to have a higher impact on the pose of the end effector. In some examples, higher weight may optionally be placed on position and/or rotation values over velocity, force and/or torque values.

At a process 340, it is determined whether the deviation is above a threshold. Deviation between the actual kinematics and/or dynamics and the desired kinematics and/or dynamics of the repositionable arm and/or the end effector is expected during control of the end effector. For example, this can occur as a result of delays in implementing motion, calibration errors in the end effector and/or computer-assisted medical device, sensor errors, manufacturing variations between different computer-assisted medical devices, vibrations in the end effectors and/or repositionable arms, movement of the patient such as due to respiration, and/or combinations of any of these and/or other factors. Thus, the threshold is optionally chosen to be larger than expected errors in determining the actual kinematic and/or dynamic values being monitored yet not so large as to create unreasonable risk of injury to the patient, injury to medical personnel, damage to the end effector, damage to the computer-assisted medical device, and/or damage to other devices and structures in proximity to the computer-assisted medical device. In some examples, the deviation for each of the kinematic and/or dynamic values is optionally separately compared to a threshold to determine whether any one of the kinematic and/or dynamic values is above the threshold. In such a case, the threshold may be a single value applicable for all of the kinematic or dynamic values, or comprise a vector or matrix of threshold elements corresponding to the kinematic and/or dynamic values. In some examples, the threshold (or threshold element) for each of the kinematic and/or dynamic values may optionally be different. In some examples, the threshold may optionally be selected and/or adjusted based on a mode of operation of the end effector, a mode of operation of the computer-assisted medical device, a type of motion being controlled by process 310, and/or the like. In some examples, the threshold may optionally be selected based on acceptable clinical deviations allowed before risk to injury of the patient is considered too high. In some examples, the threshold is set based on types and/or numbers of the kinematic and/or dynamic values used to determine deviations. In some examples, the threshold is set to a range corresponding to approximately 6-12 mm of deviation in a post of the end effector, which is typically a reasonably safe distance that an end effector may deviate from a desired pose before causing injury to the patient. When the deviation between the actual kinematics and/or dynamics and the desired kinematics and/or dynamics is not above the threshold, control of the motion of the end effector continues by repeating processes 310-340. When the deviation between the actual kinematics and/or dynamics and the desired kinematics and/or dynamics is above the threshold, halting of one or more repositionable arms and a recovery process begins with a process 350.

At the process 350, motion of one or more repositionable arms is halted. In some embodiments, the motion of the one or more repositionable arms is optionally halted as quickly as possible after the deviation in pose above the threshold is detected. In some examples, the detection of the deviation above the threshold and initiation of the halting process occurs within a single cycle of a control loop used by process 310 to control motion of the end effectors and/or repositionable arms so as to minimize further increase in the deviation in motion. In some examples, the detection of the deviation above the threshold and initiation of the halting process occurs within 1 millisecond or less of the detection of the deviation in motion above the threshold. In some examples, the detection of the deviation above the threshold and initiation of the halting process occurs within a predetermined period of time based on the current operating mode and/or type of motion being performed by each of the end effectors and/or repositionable arms.

According to some embodiments, when an unacceptable deviation between the actual kinematics and/or dynamics and the desired kinematics and/or dynamics for a repositionable arm and/or an end effector is detected by process 340, it may indicate an unacceptable inability to control the repositionable arm and/or the end effector. The deviation between the actual kinematics and/or dynamics and the desired kinematics and/or dynamics may be indicative of a collision between the repositionable arm and/or end effector and another repositionable arm and/or end effector, a collision between a repositionable arm and/or an end effector and other objects, and structures, a collision between the repositionable arm and/or end effector and the patient and/or other medical personnel, range of motion limits in the repositionable arm and/or end effector, and/or the like. Because these conditions may not be as easily detectible in each of the repositionable arms and/or end effectors of the computer-assisted medical device, motion is halted in each of the repositionable arms and/or end effectors subject to halting and recovery. This is because the condition may more quickly create a deviation in the kinematics and/or dynamics of one end effector before it creates a deviation in another. As but one of many possible examples, an end effector and its corresponding repositionable arm under teleoperated control by medical personnel may collide with an end effector and repositionable arm being held in place, which may result in a deviation between the actual kinematics and/or dynamics and the desired kinematics and/or dynamics above the threshold that is first detectable in either of the end effectors and/or repositionable arms. Further, the collision may not cause a deviation between the actual kinematics and/or dynamics and the desired kinematics and/or dynamics above a threshold in both of the end effectors and/or repositionable arms. In many operational scenarios, halting of one or both of the end effectors and/or repositionable arms and possibly other end effectors and/or repositionable arms of the computer-assisted medical device is desired when an unacceptable deviation in kinematics and/or dynamics for any end effector and/or repositionable arm is detected. Often this occurs irrespective of which of the end effectors and/or repositionable arms in which the unacceptable deviation occurs or is detected. In some embodiments, one or more end effectors and/or repositionable arms not exhibiting a deviation in kinematics and/or dynamics above the threshold are halted. In some embodiments, one or more end effectors and/or repositionable arms exhibiting a deviation in kinematics and/or dynamics above the threshold are halted. In some embodiments, only those end effectors and/or repositionable arms which have a deviation in kinematics and/or dynamics above the threshold are optionally halted, and the others are allowed to continue motion.

In some embodiments, selection of which of the end effectors and/or repositionable arms to halt may optionally depend on the current operating mode and/or type of motion being performed by each of the respective end effectors and/or repositionable arms. In some examples, any end effectors and/or repositionable arms operating in a teleoperated, autonomous, or semi-autonomous mode may optionally be halted when a deviation in pose above the threshold is detected. A desired motion of no motion is equivalent to a desired, stationary pose. In some examples, end effectors and/or repositionable arms being directed to hold in place are halted when a deviation in pose above the threshold is detected. In some examples, end effectors and/or repositionable arms that are being operated in a null space mode where a pose of a corresponding end effector is not expected to change even though redundant degrees of freedom in a corresponding repositionable arm proximal to the corresponding end effector are being manipulated to reposition a portion of the corresponding repositionable arm are halted when a deviation in kinematics and/or dynamics above the threshold is detected. In some examples, end effectors and/or repositionable arms that are being operated in an instrument removal mode where a corresponding end effector is being removed from a patient and/or is being disconnected from a cannula where the corresponding end effector is inserted into the patient are halted when a deviation in kinematics and/or dynamics above the threshold is detected.

Figure 4:
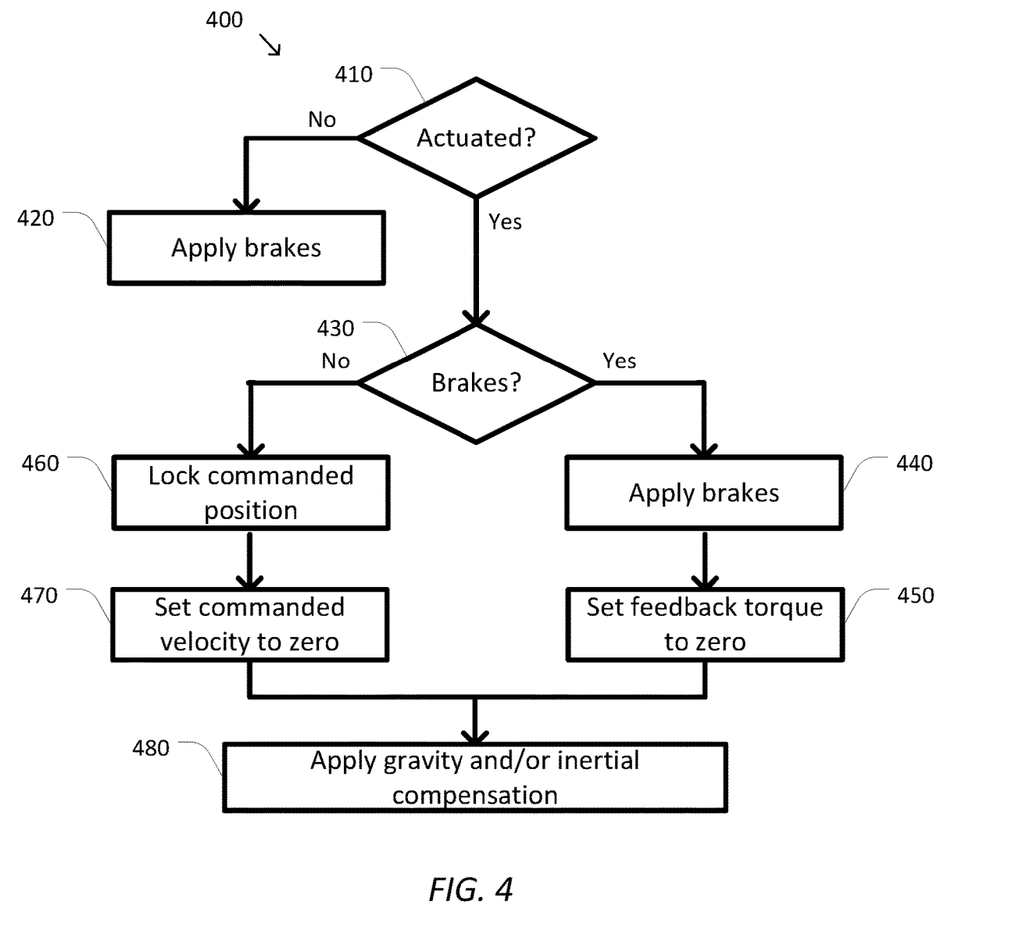
FIG. 4 is a simplified diagram of a method of halting a repositionable element in a repositionable arm and/or end effector according to some embodiments.

FIG. 4 is a simplified diagram of a method 400 of halting a repositionable element in a repositionable arm and/or end effector according to some embodiments. One or more of the processes 410-480 of method 400 may be implemented, at least in part, in the form of executable code stored on non-transient, tangible, machine readable media that when run by one or more processors (e.g., the processor 150 in control unit 130) may cause the one or more processors to perform one or more of the processes 410-480. In some embodiments, method 400 may optionally be used to halt each of the one or more repositionable elements, such as joints, of each of the one or more end effectors and/or repositionable arms that process 350 determines are to be halted as a result of the detected deviation in pose above the threshold. In some embodiments, the halting of each of the one or more repositionable elements may occur concurrently for each of the repositionable elements and/or in staggered fashion with the halting of different repositionable elements occurring at different times. According to some embodiments, the order in which processes 410-480 are performed may optionally vary from the order implied by the diagram of FIG. 4. In some examples, processes 440 and 450 and/or 460, and 470 may optionally be performed concurrently or in any order. In some examples, process 480 may optionally be applied concurrently with any of processes 440-470. In some examples, process 480 is optional and may be omitted.

At a process 410, it is determined whether a repositionable element is actuated. The approach used to halt a repositionable element, such as an articulated, rotational, and/or prismatic joint, depends on whether the repositionable element is actuated. The repositionable element is actuated when one or more actuators, such as a motor, servo, solenoid, and/or the like are usable to apply force and/or torque to the repositionable element to change its position and/or orientation. For example, a rotational joint that is coupled to a motor or servo that can be driven to change the rotation angle of the rotational joint is an actuated joint. In contrast a repositionable element equipped only with brakes or a similar mechanism to halt movement in the repositionable element is not actuated. In some examples, the actuator used to move the repositionable element may optionally be directly coupled to the repositionable element and/or indirectly coupled through one or more cables, rod, gears, cogs, and/or the like so that the actuator does not have to be located at or near the repositionable element. When the repositionable element is not actuated, movement of the repositionable element is halted by applying brakes using a process 420. When the repositionable element is actuated it is determined whether the repositionable element includes brakes using a process 430.

At the process 420, the brakes of the non-actuated repositionable element are applied. One or more signals, such as voltages, currents, pulse-width modulated signals, and/or the like are sent to the brakes of a non-actuated repositionable element in order to halt and/or significantly impede further motion in the non-actuated repositionable element. In some examples, the one or more signals may optionally cause activation of an electric, magnetic, piezo electric, hydraulic, and/or pneumatic brake that applies friction and/or a stopping force to one or more surfaces of the repositionable element. In some examples, the one or more signals may optionally cause deactivation of an electric, hydraulic, and/or pneumatic mechanism that prevents application of a brake, such as a mechanism used to counteract one or more springs that would cause application of the brake but for the activation of the electric, magnetic, piezo electric, hydraulic, and/or pneumatic mechanism. Depending upon the repositionable element, the brakes may optionally be applied gradually and/or all at once for the repositionable element. Once the brakes are applied to the non-actuated repositionable element, method 400 ends for that repositionable element.

At the process 430, it is determined whether the actuated repositionable element includes brakes. Applying brakes in an actuated repositionable element increases the likelihood that the repositionable element is halted; however, use of the brakes in an actuated repositionable element may be optional depending on the operational mode for the repositionable element. When an actuated repositionable element includes brakes the brakes are applied using a process 440. When the actuated positional element does not include brakes, halting of the actuated repositionable element continues with a process 460.

At the process 440, the brakes of the actuated repositionable element are applied using a process substantially similar to process 420 for a non-actuated repositionable element.

At a process 450, feedback torque of the actuated repositionable element is set to zero. In order to keep the actuated repositionable element from pushing against the brakes applied during process 440, the feedback torque applied to the actuated repositionable element to help drive the actuated repositionable element to its commanded position is set to zero. In some examples, the feedback torque may optionally be set to zero directly and/or indirectly by setting one or more feedback gains to zero. In some examples, the feedback gains to set to zero include a torque feedback gain and/or a combination of a position feedback gain and a velocity feedback gain. In some examples, the feedback torque and/or one or more feedback gains may optionally be set to zero immediately or set to zero using a ramp and/or a sequence of discrete steps. Once the feedback torque is removed by process 450, gravity and/or inertial compensation is optionally applied using a process 480.

At the process 460, a commanded position for the actuated repositionable element is locked. In some examples, because the actuated repositionable element is being driven to follow a motion plan and/or a motion profile, locking of the commanded position of the actuated repositionable element to its current commanded value prevents the actuated repositionable element from continuing to follow the motion plan and/or the motion profile. This, in effect, causes the actuated repositionable element to drive to the currently commanded position when the halt was initiated while also preventing a possible jump in the position of the actuated repositionable element.

At a process 470, the commanded velocity for the actuated repositionable element is set to zero. Locking the commanded position using process 460 and setting the commanded velocity of the actuated repositionable element to zero causes the control module for the one or more actuators used to actuate the actuated repositionable element to cease motion of the actuated repositionable element. Thus, the actuated repositionable element resists deviation from its current position. In some examples, the commanded velocity may optionally be set to zero immediately or set to zero using a ramp and/or a sequence of discrete steps. In some examples, a velocity feedback gain for the actuated repositionable element may optionally be set to zero instead of directly setting the commanded velocity to zero.

At an optional process 480, gravity and/or inertial compensation is applied to the actuated repositionable element. In order to compensate for the effects of gravity on the finite masses of the end effector and/or the repositionable arm, the control module for the actuated repositionable element may optionally introduce feed-forward forces and/or torques in the one or more actuators for the actuated repositionable element. In some examples, these injected forces and/or torques compensate for potential drift in the actuated repositionable element while it is being halted. Examples of control modules providing inertial and/or gravity compensation in an actuated repositionable element are described in further detail in U.S. Pat. No. 9,198,730 entitled "Control System for Reducing Internally Generated Frictional and Inertial Resistance to Manual Positioning of a Surgical Manipulator," which is hereby incorporated by reference in its entirety.

As discussed above and further emphasized here, FIG. 4 is merely an example which should not unduly limit the scope of the claims. One of ordinary skill in the art would recognize many variations, alternatives, and modifications. In some embodiments, use of brakes on actuated repositionable elements with brakes is optional so that an actuated repositionable element with brakes may optionally be halted using processes 460 and 470, thus omitting processes 430-450.

Referring back to FIG. 3, at a process 360 the halt is cleared. In some embodiments, it is generally desirable to rapidly clear the condition that caused the deviation in motion above the threshold to occur. In some examples, clearing the condition that caused the deviation in motion above the threshold may optionally include setting a commanded position for one or more repositionable elements to a current position of the one or more repositionable elements. In some examples, clearing of the condition that caused the deviation in motion above the threshold may optionally involve intervention by one or more medical personnel operating the computer-assisted medical device. In some examples, the computer-assisted medical device may optionally provide feedback and/or instructions to the medical personnel on how to clear the condition that caused the deviation in motion above the threshold. In some examples, the feedback and/or instructions may optionally include the computer-assisted medical device providing one or more audio and/or visual alerts to the one or more medical personnel. In some examples, the alerts may optionally include an alert that one or more of the end effectors and/or repositionable arms has been halted during process 350, an identification of which of the end effectors and/or repositionable arms has been halted, one or more instructions on how to clear the condition causing the halt, and/or the like. In some examples, the alerts may optionally include making one or more sounds such as a designated alert tone, lighting and/or flashing one or more indicator lights signifying a halt alert, issuing one or more verbal instructions for clearing the condition causing the halt, sending one or more messages and/or instructions for clearing the condition causing the halt to a status and/or operational display unit such as a display unit in the operator console, and/or the like. In some examples, the alert may optionally be issued as soon as or shortly after the corresponding end effector and/or repositionable arms is halted during process 350.

In some embodiments, the form and/or content of the alert may optionally vary based on the current operating mode and/or type of motion being performed by each of the halted end effectors and/or repositionable arms. In some examples, the content of the alert may optionally be varied to provide mode-specific instructions for clearing the condition causing the halt of a corresponding end effector and/or repositionable arm. In some examples, when a corresponding end effector and/or repositionable arm is being operated in a null space mode, the alert may optionally include instructing the one or more medical personnel to deactivate one or more input controls used to activate and/or enter the null space mode, cancel a command placing the corresponding end effector and/or repositionable arm in the null space mode, and/or the like. In some examples, when a corresponding end effector and/or repositionable arm is being operated in an instrument removal mode the alert may optionally include instructing the one or more personnel to deactivate one or more input controls used to activate and/or enter the instrument removal mode and/or to manually remove the instrument from the patient and/or the cannula through which the instrument and end effector are inserted.

After the condition causing the halt for each of the halted end effectors and/or repositionable arms is cleared, motion of the end effectors and/or repositionable arms based on their respective current operating modes and/or types of motion resumes by returning to process 310.

As discussed above and further emphasized here, FIG. 3 is merely an example which should not unduly limit the scope of the claims. One of ordinary skill in the art would recognize many variations, alternatives, and modifications. In some embodiments, end effectors and/or repositionable arms not subject to halting due to their respective operating modes, types of motion, and/or other factors are not affected by processes 350 and 360 and may continue to cycle through processes 310-340 allowing their respective motions to proceed even though one or more other end effectors and/or repositionable arms of the computer-assisted medical device remain in the halt condition instituted during process 350.

Some examples of control units, such as control unit 130 may include non-transient, tangible, machine readable media that include executable code that when run by one or more processors (e.g., processor 150) may cause the one or more processors to perform the processes of methods 300 and/or 400. Some common forms of machine readable media that may include the processes of methods 300 and/or 400 are, for example, floppy disk, flexible disk, hard disk, magnetic tape, any other magnetic medium, CD-ROM, any other optical medium, punch cards, paper tape, any other physical medium with patterns of holes, RAM, PROM, EPROM, FLASH-EPROM, any other memory chip or cartridge, and/or any other medium from which a processor or computer is adapted to read.

Although illustrative embodiments have been shown and described, a wide range of modification, change and substitution is contemplated in the foregoing disclosure and in some instances, some features of the embodiments may be employed without a corresponding use of other features. One of ordinary skill in the art would recognize many variations, alternatives, and modifications. Thus, the scope of the invention should be limited only by the following claims, and it is appropriate that the claims be construed broadly and in a manner consistent with the scope of the embodiments disclosed herein.

What is claimed is:

1. A computer-assisted device comprising:
   a first repositionable arm, the first repositionable arm configured to support a first end effector;
   a second repositionable arm, the second repositionable arm configured to support a second end effector; and
   a control unit communicably coupled to the first repositionable arm and the second repositionable arm, wherein the control unit is configured to at least:
     monitor an actual motion of at least one structure selected from the group consisting of the first repositionable arm and the first end effector;
     determine a deviation threshold based on at least one mode of operation selected from the group consisting of: a mode of operation of the first end effector and a mode of operation of the computer-assisted device; and
     in response to determining that the actual motion of the at least one structure deviates from a desired motion of the at least one structure by more than the deviation threshold, halt motion of the first repositionable arm and the first end effector or halt motion of the second repositionable arm and the second end effector.

2. The computer-assisted device of claim 1, wherein the mode of operation of the first end effector is selected from the group consisting of: an autonomous motion mode, a semi-autonomous motion mode, a null space motion mode, an instrument removal mode, and a fixed pose mode in which the first end effector is held at a fixed pose.

3. The computer-assisted device of claim 1, wherein the mode of operation of the computer-assisted device comprises a teleoperated mode.

4. The computer-assisted device of claim 1, wherein to halt motion of the first repositionable arm and the first end effector or to halt motion of the second repositionable arm and the second end effector, the control unit is configured to:
   select whether to halt motion of the first repositionable arm and the first end effector or to halt motion of the second repositionable arm and the second end effector based on at least one mode of operation selected from the group consisting of: the mode of operation of the first repositionable arm and the mode of operation of the first end effector.

5. The computer-assisted device of claim 1, wherein to monitor the actual motion of the at least one structure, the control unit is configured to determine a position of a portion of the first end effector.

6. The computer-assisted device of claim 1, wherein to determine whether the actual motion of the at least one structure deviates from the desired motion of the at least one structure by more than the deviation threshold, the control unit is configured to:
   determine a composite deviation in a plurality of kinematic or dynamic values, the plurality of kinematic or dynamic values associated with the first repositionable arm or the first end effector.

7. The computer-assisted device of claim 6, where to determine the composite deviation, the control unit is configured to:
   determine, for each kinematic or dynamic value in the plurality of kinematic or dynamic values, a difference between an actual value and a corresponding desired value to generate a combined set of variation values; and
   determine, from the combined set of variation values, the composite deviation.

8. The computer-assisted device of claim 1, further comprising:
   an input device; wherein the control unit is further configured to receive a command from the input device indicating the desired motion of the at least one structure.

9. The computer-assisted device of claim 1, wherein:
   to halt motion of the first repositionable arm and the first end effector, the control unit is configured to:
     halt motion of one or more first repositionable elements for positioning the first repositionable arm, or
     set a commanded position of an actuated first repositionable element of the one or more first repositionable elements to a current commanded position of the actuated first repositionable element, and set a commanded velocity of the actuated first repositionable element to zero; and
   to halt motion of the second repositionable arm and the second end effector, the control unit is configured to:
     halt motion of one or more second repositionable elements for positioning the second repositionable arm, or
     set a commanded position of an actuated second repositionable element of the one or more second repositionable elements to a current commanded position of the actuated second repositionable element, and set a commanded velocity of the actuated second repositionable element to zero.

10. The computer-assisted device of claim 1, wherein:
    to halt motion of the first repositionable arm and the first end effector, the control unit is configured to:
      apply a brake of an actuated first repositionable element of one or more first repositionable elements for positioning the first repositionable arm, and
      set a feedback torque for the actuated first repositionable element to zero; and
    to halt motion of the second repositionable arm and the second end effector, the control unit is configured to:
      apply a brake of an actuated second repositionable element of one or more second repositionable elements for positioning the second repositionable arm, and
      set a feedback torque for the actuated second repositionable element to zero.

11. The computer-assisted device of claim 1, wherein the desired motion of the at least one structure is no motion of the at least one structure.

12. The computer-assisted device of claim 1, wherein the control unit is further configured to clear a condition that caused the actual motion of the at least one structure to deviate from the desired motion of the at least one structure by more than the deviation threshold.

13. A method comprising:
monitoring, by a control unit of a computer-assisted device, an actual motion of at least one structure, the at least one structure selected from the group consisting of: a first repositionable arm of the computer-assisted device, and a first end effector configured to be supported by the first repositionable arm;
determining, by the control unit, a deviation threshold based on at least one mode of operation selected from the group consisting of: a mode of operation of the first end effector and a mode of operation of the computer-assisted device; and
halting, by the control unit and in response to determining that the actual motion of the at least one structure deviates from a desired motion of the at least one structure by more than the deviation threshold, motion of the first repositionable arm and the first end effector or motion of a second repositionable arm of the computer-assisted device.

14. The method of claim 13, wherein the mode of operation of the first end effector is selected from the group consisting of: an autonomous motion mode, a semi-autonomous motion mode, a null space motion mode, an instrument removal mode, and a fixed pose mode in which the first end effector is held at a fixed pose.

15. The method of claim 13, wherein halting motion of the first repositionable arm and the first end effector or motion of the second repositionable arm of the computer-assisted device comprises:
selecting, by the control unit, whether to halt motion of the first repositionable arm and the first end effector or to half motion of the second repositionable arm based on at least one mode of operation selected from group consisting of: the mode of operation of the first repositionable arm and the mode of operation of the first end effector.

16. The method of claim 13, wherein monitoring the actual motion of the at least one structure comprises determining a position of a portion of the first end effector.

17. The method claim 13, wherein determining whether the actual motion of the at least one structure deviates from the desired motion of the at least one structure by more than the deviation threshold comprises:
determining a composite deviation in a plurality of kinematic or dynamic values, the plurality of kinematic or dynamic values associated with the first repositionable arm or the first end effector.

18. The method of claim 13, wherein halting motion of the first repositionable arm and the first end effector comprises:
halting motion of one or more repositionable elements for positioning the first repositionable arm; or
setting a commanded position of an actuated repositionable element of the one or more repositionable elements to a current commanded position of the actuated repositionable element, and setting a commanded velocity of the actuated repositionable element to zero; or
applying a brake of the actuated repositionable element, and setting a feedback torque for the actuated repositionable element to zero.

19. A non-transitory machine-readable medium comprising a plurality of machine-readable instructions which when executed by one or more processors associated with a computer-assisted device are adapted to cause the one or more processors to perform a method comprising:
monitoring an actual motion of at least one structure, the at least one structure selected from the group consisting of: a first repositionable arm of the computer-assisted device, and a first end effector configured to be supported by the first repositionable arm;
determining a deviation threshold based on at least one mode of operation selected from the group consisting of: a mode of operation of the first end effector and a mode of operation of the computer-assisted device; and
halting, in response to determining that the actual motion of the at least one structure deviates from a desired motion of the at least one structure by more than the deviation threshold, motion of the first repositionable arm and the first end effector or motion of a second repositionable arm of the computer-assisted device.

20. The non-transitory machine-readable medium of claim 19, wherein halting motion of the first repositionable arm and the first end effector or motion of the second repositionable arm of the computer-assisted device comprises:
selecting whether to halt motion of the first repositionable arm and the first end effector or to half motion of the second repositionable arm based on at least one mode of operation selected from group consisting of the mode of operation of the first repositionable arm and the mode of operation of the first end effector.

* * * * *

UNITED STATES PATENT AND TRADEMARK OFFICE
CERTIFICATE OF CORRECTION

PATENT NO. : 11,779,415 B2
APPLICATION NO. : 17/569405
DATED : October 10, 2023
INVENTOR(S) : Goran A. Lynch, Paul G. Griffiths and Michael Turner

Page 1 of 1

It is certified that error appears in the above-identified patent and that said Letters Patent is hereby corrected as shown below:

On the Title Page (63) Related U.S. Application Data:
Please delete "Continuation of application No. 16/069,875, filed as application No. PCT/US2016/067755 on Dec. 20, 2016, now Pat. No. 11,246,669." and insert --Continuation of application No. 16/069,875, filed on Jul. 12, 2018, now Pat. No. 11,246,669, which is a 371 of application No. PCT/US2016/067755, filed on Dec. 20, 2016.--.

Signed and Sealed this
Seventh Day of November, 2023

Katherine Kelly Vidal
*Director of the United States Patent and Trademark Office*